United States Patent [19]

Good

[11] 4,027,954

[45] June 7, 1977

[54] EYE-TESTING APPARATUS

[75] Inventor: Carleton R. Good, Addison, Ill.

[73] Assignee: School Health Supply Company, Addison, Ill.

[22] Filed: Feb. 10, 1975

[21] Appl. No.: 548,383

[52] U.S. Cl. .................................. 351/17; 351/36; 351/37

[51] Int. Cl.² ......................................... A61B 3/02

[58] Field of Search .................. 351/17, 32, 36, 37, 351/14

[56] References Cited

UNITED STATES PATENTS

| | | | |
|---|---|---|---|
| 2,364,793 | 12/1944 | Jobe et al. | 351/36 |
| 3,012,472 | 12/1961 | Feinberg | 351/36 |
| 3,519,338 | 7/1970 | Papritz | 351/14 X |

Primary Examiner—Paul A. Sacher
Attorney, Agent, or Firm—Burmeister, York, Palmatier, Hamby & Jones

[57] ABSTRACT

A device for testing eyes provided with a rotatable drum located within a light impermeable casing in which the drum carries a plurality of slides bearing characters positioned on the perimeter of the drum and illuminated by a lamp located within the drum, and in which the characters may be viewed by the person whose eyes are being tested through an optical system. The optical system has a direct path to a near testing station on the drum for near vision testing, and a longer indirect path to a far vision testing station on the drum utilizing a mirror positioned perpendicularly to the far vision testing station to increase the path length. The eye testing apparatus has an aperture in a sidewall of the casing located between the drum and the reflector adjacent to the far testing station to permit the operator to directly view the slide at the far test station in which an optical system is provided for the operator which includes a convex lens at the aperture and a mirror mounted between the drum and the reflector adjacent to the opposite sidewall of the casing in order to improve the visibility and illumination of the characters on the slide as seen by the operator.

1 Claim, 3 Drawing Figures

EYE-TESTING APPARATUS

The present invention relates to eye-testing apparatus and in particular to such apparatus in which a person operating the apparatus may view the same test object as viewed by the person whose vision is being tested.

Eye-testing apparatus in which the person whose eyes are to be tested views one or more eye-testing charts through an optical system are well known. U.S. Pat. No. 3,012,472 of Richard Feinberg and Reuel A. Sherman entitled "EYE TESTING APPARATUS" is an example of such equipment. In use, the operator of the equipment generally requires the person whose eyes are to be tested to read back lines of figures or numbers located on charts within the device. The operator must be able to see the same chart as the person whose eyes are being tested, and the operator often desires to point to a particular character on the chart. In the device of U. S. Pat. No. 3,012,472, a plurality of charts are mounted on a drum, and the charts may be viewed through a two position optical system. In one position, the optical system directly views one of the charts located in a position referred to as the near testing station for the purpose of testing the near vision of the person. In the other position of the optical system, the person whose eyes are to be tested views a chart in a second position known as the far vision testing station through an elongated path which includes a reflector positioned substantially perpendicularly to the chart at the far vision testing station. Accordingly, the housing for the eye-testing apparatus of Feinberg cannot be provided with apertures directly viewing the far testing station due to the position of the reflector, and an aperture is provided in one of the sidewalls for this purpose. A pointer may also be inserted through the aperture in the sidewall. Further, apertures cannot be provided in the apparatus of Feinberg to perpendicularly view the chart at the near vision testing station since the optical system itself confronts this chart. Hence, for both the near and far vision testing stations of the Feinberg device, the operator is compelled to view the charts through a narrow angle through apertures in the sidewall of the apparatus.

Accordingly, eye-testing apparatus of the type described in the Feinberg patent does not provide charts readily visible to the operator, resulting in operator error and confusion. Further, since the charts of such devices are transparent and illuminated by a lamp within the device, little illumination is available to the operator due to the small angle at which the operator views the test charts.

It is an object of the present invention to provide an eye-testing apparatus which achieves improved visibility of the eye-testing charts by the operator.

In addition, it is an object of the present invention to provide an eye-testing apparatus in which the operator may more readily point to the individual characters in the eye-testing charts of the apparatus.

In accordance with the present invention, a vision testing apparatus is provided in which a transparent slide is viewed by the person whose vision is being tested at a far vision testing station through an optical system utilizing a light reflector confronting the slide, the slide being mounted on an illuminated drum within a light impermeable housing, and the operator is provided with an optical system for viewing the same slide at the far vision testing station which includes a second light reflector mounted within the housing between the drum and the first light reflector at one end of the drum and confronting an aperture in the housing at the other end of the drum. Further, the illumination of the characters on the slide visible to the operator is increased by a converging lens at the aperture.

The objects of the present invention will become further apparent from the detailed description of a preferred embodiment of the invention given hereinafter, particularly with reference to the drawings, in which.

Figure 1:
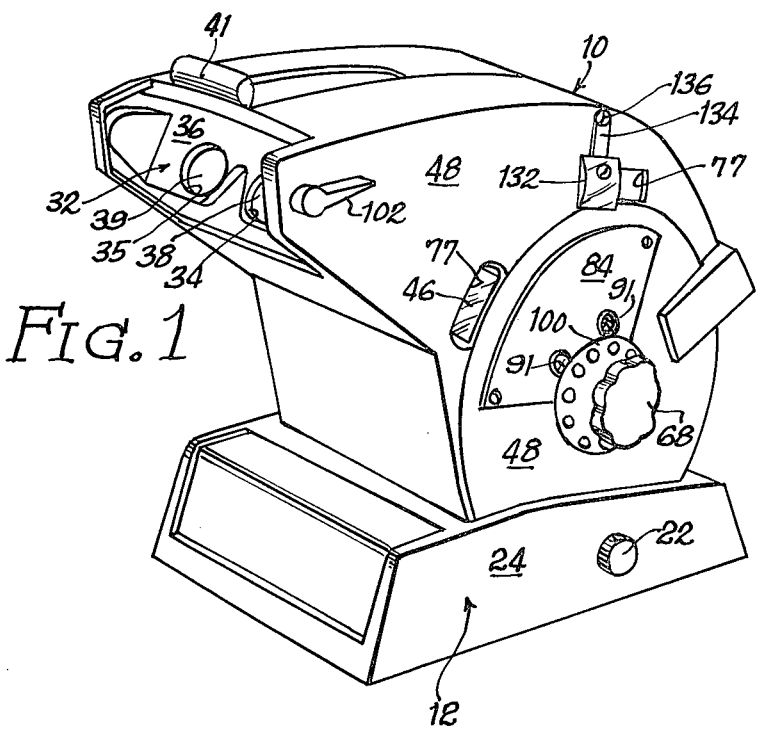
FIG. 1 is a perspective view of an eye-testing apparatus embodying the present invention.

Referring to the drawings, the numeral 10 represents a light impermeable casing rotatably mounted in the base 12. The casing 10 may be adjustably elevated or depressed with respect to the base member 12 so that the device may be suitably positioned before the eyes of a person undergoing tests. The casing 10 rests upon a set of guide rollers 14 which are carried by an axle 15 rotatably mounted in the base member 12. The rollers 14 are arranged to register with a guideway 16 formed in the rounded lower portion 18 of the casing 10. A tension spring 20 for balancing the casing 10 in an adjusted position of elevation is provided and has one end secured to the base member 12 and the other end secured to the lower portion 18 of the casing 10 for resiliently urging the casing 10 in a clockwise direction. A tension control knob 22 is connected to a shaft 23 which passes through the sidewall 24 of the base member 12 and a slot 26 disposed in a sidewall 48 of the casing. A lug 28 is threadedly secured to the shaft 23 for frictionally controlling the rotary movement of the casing 10 in relation to the base member 12. Accordingly, tension on the shaft 23 may be varied by turning the knob 22 for balancing the force exerted by the spring 20.

An opening 30 is disposed in the front of the casing 10 exposing a viewing means 32. The viewing means 32 comprises a viewing frame 36 having right and left hand openings 34 and 35 formed in the viewing frame for receiving lenses 38 and 39, respectively, which serve to focus on the test targets at desired optical test distances. The viewing frame 36 is pivotally mounted to the casing 10 by means of pins 40. A forehead rest 41 is mounted on the housing 10 above the lens frame 36, and the forehead rest is adapted to accommodate the observer's head when taking a test.

A drum 42 is rotatably supported within the casing 10 on a suitably journalled shaft 44 which is positioned between the sidewalls 48 and 50 of the casing. The drum 42 is rotatable about an axis transversely disposed with respect to the sidewalls 48 and 50 and perpendicular thereto. Drum 42 comprises a central circular disc 52 supported on a hub 54 which is connected to the shaft 44 by means of a key 45. The shaft 44 passes through the sidewalls 48 and 50 of the casing 10. The end of the shaft 44 is directly connected to a manual selector knob 68 which permits manual rotation of the drum 42 and also provides an index visible from the exterior of the apparatus.

The central circular disc 52 supports a plurality of transparent target slides or test objects 46 of different types suitable for testing either far point or near point vision characteristics. Since the target slides employed for testing far point vision are entirely different than the type used to test near point vision, it is desirable to be able to move each individual stereo slide through a related testing station in any desired sequence or combination regardless of its position on the drum by rotating the central circular disc a predetermined amount by rotating the knob. The transparent test objects 46 are carried by corresponding holders 70 which are equally spaced about the perimeter of a disc 52.

Each holder 70 includes a rectangular seat 72 which defines a rectangular aperture 75 which permits illumination of the test objects 46. Each slide 46 has a rectangular shape and is supported by the seat 72. One side of each seat 72 has a substantially flat surface 73 on which the bottom longitudinal edge of a target slide 46 is seated while the adjoining side of the same seat is provided with a flange 71 defining a channel under which an adjacent slide is engaged. The other bottom longitudinal edge of the slide abuts against a felt or rubber pad 69 secured to the rear inclined surface of flange 71. Test objects 46 are removable retained in mounted position by an elastic retaining band 67 which extends around the periphery of drum 42 and engages the top surface of each slide. Each individual slide holder 70 is secured to the centrally located circular disc 52 by means of a depending flange 76. The interchangeable stereo test slides 46 can be mounted in any sequence or removed from the holders 70 by passing them through an opening 127 located at the rear of the casing 10 which is normally closed by an access cover 128.

Figure 2:
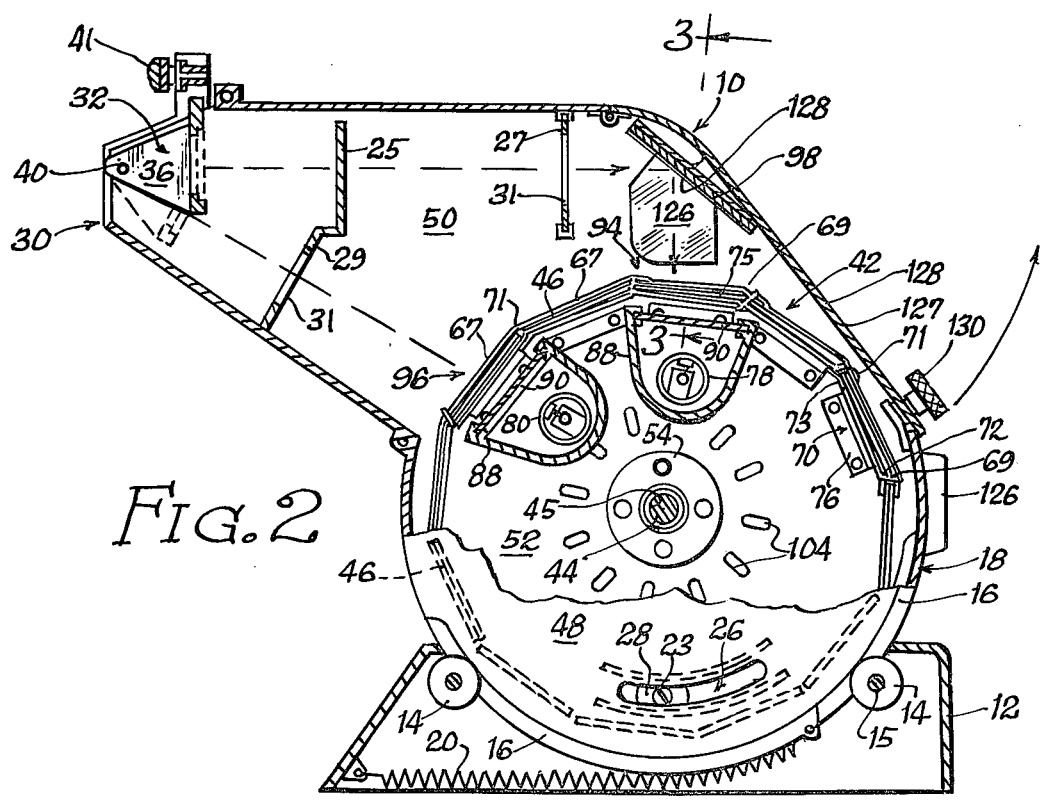
FIG. 2 is a longitudinal sectional view of the device shown in FIG. 1.

Illuminating means in the form of separate pairs of electric lamps 78 and 80 are mounted within the drum, FIG. 2 illustrating one lamp of each pair, the other lamp being mounted in identical manner on the opposite side of the central circular disc 52. Separate lenses 91, illustrated in FIG. 1, disposed in an adaptor plate 84 covering an aperture in the wall 48 (not shown) confronts each lamp 78 and 80 to visually indicate to the operator when one of the lamps is illuminated and, consequently, when a selected set of test objects 46 are located in a related testing station.

The lamps 78 and 80 are enclosed in separate pairs of right and left housings, the right housings 88 being illustrated in FIG. 2 and the left housings being identical in construction. A window 90 is attached to each of the housings 88 in front of the light source and is formed of translucent material for equally diffusing the emitted illumination from the lamps 78 or 80. The windows 90 are located directly behind the rectangular aperture 75 formed in the seat 72 so as to uniformly frame and illuminate the test objects 46 when they are in viewing position. The housings 88 adjacent to the lamp 80 define a test station 96 for near point vision, while the housings 88 adjacent to the lamp 78 define a test station 94 for far point vision characteristics. The near point test vision station 96 exposes the windows 90 which are positioned in alignment with the viewing means 32 carried at the front of the casing 10 so that any related near point test target slide 46 aligned with these windows may be directly observed, the plane of the slides before the windows being substantially normal to the line of sight. On the other hand, the far point vision test station 94 exposes windows 90 positioned in alignment with an optical reflector or mirror 98 which in turn is visually aligned with the viewing means 32, so that the plane of any related test object or target slide 46 aligned with these windows will be substantially normal to the line of sight. FIG. 2 indicates the line of sight for the far test position 94 and for the near test position 96.

A suitable position indicating dial 100, integrally associated with the selector knob 68, is employed to designate by the position of the dial 100 with respect to the visual indicating lenses 91 which one of the test objects is in position for observation. For viewing test objects, the pivotally mounted viewing frame 36 can be selectively positioned at an angle of about 15° below the horizontal, which is approximately the normal line of sight, or at an angle of about 45° below the horizontal, by moving an operating handle 102 which will rotate the lens frame 36 about pivot pins 40 into alignment with either far or near point test stations 94 and 96, respectively.

An upper, transversely extending divider member 27 is disposed between the viewing means 32 and the optical reflector 98, while a lower, transversely extending divider member 29 is positioned between the viewing means 32 and the near point test station 96. Both divider members 27 and 29 have a pair of openings 31 which are aligned with lenses 38 and 39, and serve as separate apertures for defining the field of vision. To facilitate fusion of the stero target slides 46, a septum 25 extends upwardly from the lower divider member 29 for merging the test object components located at the far point test station 94.

In operation, the casing 10 is elevated or depressed with respect to the base member 12 until the lenses 38 and 39 in the viewing frame 36 are opposite the eyes of the observer. The viewing means 32 is selectively positioned to conduct a far point visual test when the viewing frame 36 is aligned with the optical reflector 98. When the hand lever 102 is in this position, the lights 78 which illuminate the far point vision station 94 are energized. The drum 42 may be advanced by the knob 68 to align the far vision test object 46 with the display openings or windows 90 defined by the housing 88. In this manner, each related test object 46 is selectively brought before the eyes of the observer by controlled rotation of the drum 42.

The operator must know what vision test objects 46 are visible to the person whose vision is being examined. For this purpose, an observation aperture 77 is formed in the sidewall 48 of the casing 10 above both the far point and the near point vision test stations 94 and 96. The operator may insert a pointer in either of the apertures 77 in order to point to a particular character on the vision test object 46, and the pointer may extend to either the right eye or left eye character of the vision test object.

In practice, it has been found difficult for the operator to locate a particular character under vision test object 46, particularly a test object which is relatively remote from the aperture 77. This difficulty is due in part to the fact that the illumination from the lamps 78 or 80 is substantially perpendicular to the plane of the test object 46, so very little light is transmitted from the test object through the narrow angle between the aperture 77 and the plane of the test objects. From point of view of the person observing the test objects through the viewing means 32, the light passing through the vision test objects 46 is on an axis to maximize illumination, but from the point of view of the operator, the axis of vision loses most of the illumination.

Figure 3:
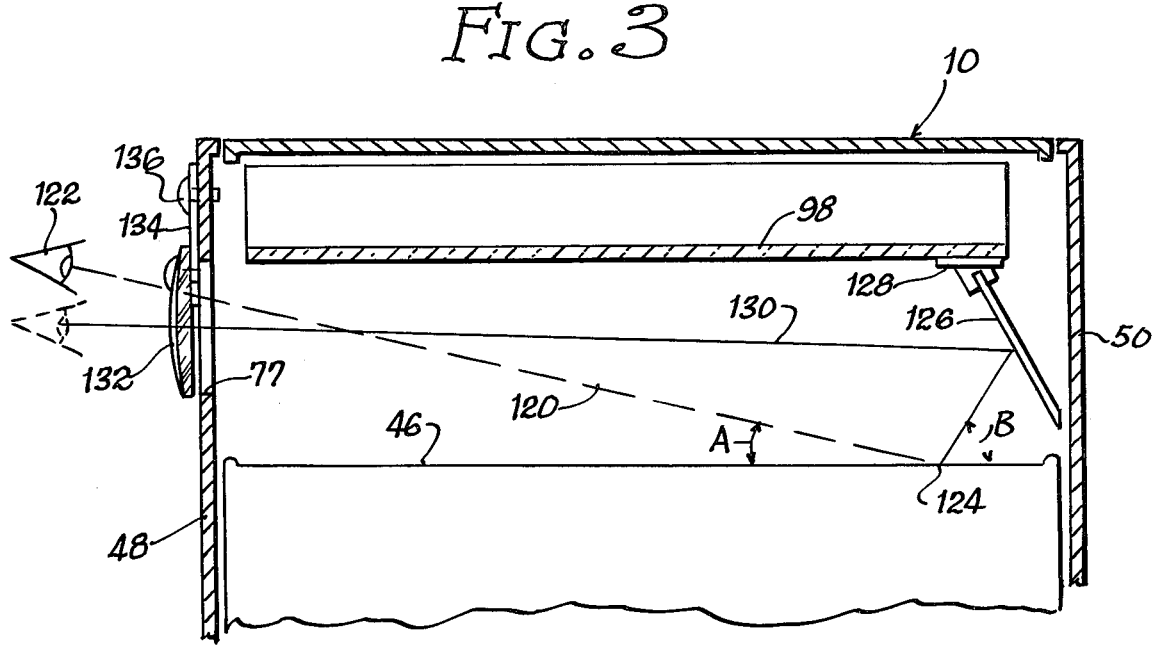
FIG. 3 is a sectional view taken along the line 3—3 of FIG. 2.

The difficulty in observing a character on the far test object 46 is illustrated in FIG. 3 by the dashed line 120 which extends from the eye 122 of the operator to the point 124 under observation. The angle between the surface of the test object 46 and the line 120, designated A, is shown to be very small.

In order to improve the angle between the line of vision and the surface of the test object 46, a reflecting mirror 126 is mounted adjacent to the side member 50 at the end of the reflector 98. The mirror 126 is secured on the end of the reflector 98 and has a flat edge 128 for this purpose. The mirror is disposed at an angle with respect to the plane of the reflector 98 and at an angle with respect to the sidewall 50. Hence, the character 124 of the vision test object 46 may be viewed through the aperture 77 along the ray 130 which is reflected by the mirror 126 to impinge upon the character 124, and it will be noted that the angle between the ray 130 from the mirror 126 to the character 124 and the surface of the test object 146, designated B, is significantly greater than the angle designated A. Hence, more light will be transmitted along the ray 130 than is transmitted along the ray 120.

In addition, a convex lens 132 is mounted on the exterior of the side member 48 confronting the far vision aperture 77 by means of a support arm 134 and bolt 136. The lens 132 increases the amount of light transmitted from the character 124 to the observation position since it bends light rays toward the central axis of the lens.

The closer the character 124 of the vision test object 46 is to the sidewall 50, the more effective is the mirror 120 and lens 132 in improving the illumination of the test character seen by the operator. If the test character 124 is close to the opposite sidewall 48, the test character may be viewed directly through the aperture 77 more readily and with greater illumination than by means of a ray reflected from the mirror 126. However, even if the character 124 is disposed close to the sidewall 48, the lens 132 will aid in collecting additional light along the direct ray illustrated in FIG. 3 by the dashed line 120.

It will be noted that the lens 132 not only can be pivoted out of alignment with the aperture 77 to permit direct viewing, or the insertion of a pointer, but the lens 132 also only partially covers the aperture 77. In this manner, the operator may insert a pointer in the aperture while viewing a character of the test object 46 by reflection from the mirror 126.

With respect to the far vision test object 46, direct viewing of the character 124 along a ray substantially perpendicular thereto is not permissible due to the presence of the reflector 98. It is thus necessary that the viewing aperture 77 be disposed in one of the sidewalls 48 or 50, or at a very small angle with respect to the surface of the far vision test object 46 in the rear wall of the housing 10. Hence the mirror 126 in lens 132 substantially improves the visibiltiy of the vision test object 46 for the operator.

While it has not been illustrated, a mirror and lens may also be used to improve the visibility of the near test object 46 through the other aperture 77. Further, those skilled in the art will find other constructions in which to utilize the present invention. It is therefore intended that the scope of the present invention not be limited by the foregoing specification, but rather only by the appended claims.

The invention claimed is:

1. Vision testing apparatus of the type adapted to test both far and near vision characteristics comprising: a base, light-occluding casing carried by said base having substantially parallel spaced walls extending from the base, a drum disposed in said casing and rotatable on an axis normal to said walls, means for rotating said drum, said casing having a far vision station and a near vision station disposed along separate portions of the drum periphery, a plurality of transparent far point and near point test objects carried by said drum in position to be selectively moved into alignment with a related test station, a light source disposed within the drum, viewing means carried by said casing including lens means adapted for optical alignment with said test objects located at either of said test stations, a reflector disposed confronting said far vision station and intermediate said viewing means and said far vision station for defining an angulated visual path therebetween which substantially increases the visual distances between said viewing means and said far vision station while reducing the physical distance therebetween, said viewing means being selectively operated between a first position in alignment with said reflector for viewing far point test objects aligned with said far vision station and a second position for viewing said near point test objects aligned with said near vision station, said near vision station being disposed intermediate said viewing means and said far vision station, and an aperture disposed in one wall of the casing between the far vision station and the reflector to permit an operator to view the test object disposed at the far vision station, characterized by the improved construction wherein a second viewing means is mounted on the casing, said second viewing means is mounted on the casing, said second viewing means having an optical path extending through the aperture substantially parallel to the axis of rotation of the drum and including a second light reflector positioned in said optical path adjacent to the other wall for reflecting the path onto the far vision station and wherein the second viewing means includes a convex lens mounted on the casing adjacent to the aperture.

* * * * *

UNITED STATES PATENT OFFICE
CERTIFICATE OF CORRECTION

Patent No. 4,027,954　　　　　　　　　Dated June 7, 1977

Inventor(s)　Carleton R. Good

It is certified that error appears in the above-identified patent and that said Letters Patent are hereby corrected as shown below:

Column 3, line 23, "removable" should read -- removably --.

Column 6, lines 47 and 48, after "casing," delete

"said second viewing means is mounted on the casing,".

Signed and Sealed this twenty-third Day of August 1977

[SEAL]

Attest:

RUTH C. MASON
*Attesting Officer*

C. MARSHALL DANN
*Commissioner of Patents and Trademarks*